United States Patent [19]

Takahashi

[11] Patent Number: 5,633,469

[45] Date of Patent: May 27, 1997

[54] BONDING LOAD MEASURING DEVICE

[75] Inventor: Iwao Takahashi, Musashimurayama, Japan

[73] Assignee: Kabushiki Kaisha Shinkawa, Tokyo, Japan

[21] Appl. No.: 547,274

[22] Filed: Oct. 24, 1995

Related U.S. Application Data

[63] Continuation of Ser. No. 279,295, Jul. 22, 1994, abandoned.

[30] Foreign Application Priority Data

Jul. 26, 1993 [JP] Japan ................... 5-202485

[51] Int. Cl.$^6$ .................................................. G01N 19/04
[52] U.S. Cl. ................................................. 73/827; 73/828
[58] Field of Search .............................. 73/817, 826, 827, 73/828

[56] References Cited

U.S. PATENT DOCUMENTS

| | | | |
|---|---|---|---|
| 2,136,344 | 11/1938 | Kochheiser et al. | 73/828 |
| 3,572,108 | 3/1971 | McShane et al. | 73/827 |
| 3,580,065 | 5/1971 | Strittmater et al. | 73/827 |
| 3,724,265 | 4/1973 | LaValle | 73/827 |
| 3,945,248 | 3/1976 | West | 73/827 |
| 4,438,880 | 3/1984 | Smith et al. | 228/1 A |
| 4,628,741 | 12/1986 | Cable | 73/826 |
| 4,817,848 | 4/1989 | Gabaldon | 228/102 |
| 4,895,028 | 1/1990 | Mayer | 73/827 |
| 4,907,458 | 3/1990 | Biggs et al. | 73/827 |

*Primary Examiner*—Richard Chilcot
*Assistant Examiner*—Eric S. McCall
*Attorney, Agent, or Firm*—Koda and Androlia

[57] ABSTRACT

A device for measuring the bonding load of the bonding arm of a bonding machine including a frame body, a screw shaft rotatably installed in the frame body, a turning member for turning the screw shaft by hand, a screw assembly screw-engaged on the screw shaft so as to be movable on the screw shaft when the screw shaft is rotated, a slider connected to the screw assembly, a gauge holder provided on the slider for installing a tension gauge, a lifting member attached to the tension gauge so that the engagement part of the lifting member can engage with the bonding arm, and a mounting assembly for mounting the frame body to the wire bonding machine.

1 Claim, 4 Drawing Sheets

BONDING LOAD MEASURING DEVICE

This is a continuation of application Ser. No. 08/279,295, filed Jul. 22, 1994, now abandoned.

BACKGROUND OF THE INVENTION

1. Field of the Invention

The present invention relates to a device for measuring the bonding load in a wire bonding machine.

2. Prior Art

In wire bonding machines, bonding wires are passed through capillaries which are attached to the tip of bonding arms and then pressed against the electrodes of semiconductor pellets and the leads of an outer lead frame so that bonding is performed between the electrodes and the leads in order to connect them. Thus, the bonding load with which the capillaries press the wires against the electrodes and leads have a great deal of effect on the quality of bonding. It is, therefore, necessary to measure and know the bonding load so that the bonding load is set as a predetermined appropriate value.

Conventionally, the measurement of the bonding load is performed using a tension gauge as shown in FIG. 6.

A wire 50 having a loop 50a at one end thereof is attached to the measuring lever 34 of the tension gauge 31. The loop 50a is hooked on the capillary fastening screw 7 which attaches the capillary 6 to the bonding arm 5, and then the tension gauge 31 held in hand is pulled upward. The bonding load is thus read from the scale of the tension gauge 31. If the read value is not equal to a set value, the bonding load is adjusted by increasing and decreasing the voltage of a linear motor which applies the bonding load to the bonding arm 5.

Thus, in the prior art, the bonding load is measured by a hand-held tension gauge 31. However, hands tend to be unstable when holding a gauge, and it is likely that measurement differs from person to person. Thus, the reliability of the measured value tends to be low. Furthermore, since the stable measurement value cannot be obtained easily, it takes a considerable period of time to adjust the bonding load to a set value.

SUMMARY OF THE INVENTION

Accordingly, the object of the present invention is to provide a bonding load measuring device which improves the reliability of the measured value of the bonding load, thus shortening the time required for setting the bonding load.

The above-described and other objects of the present invention are accomplished by a unique structure for a bonding load measuring device used in a bonding machine, and the measuring device comprises: a frame body; a screw shaft rotatably supported in the frame body; a turning member for turning the screw shaft by hand; a screw assembly provided on the screw shaft so as to be moved up and down when the screw shaft is rotated; a slider which is connected to and can be moved up and down along with the screw assembly; a gauge holder attached to the slider; a tension gauge which is installed in the gauge holder and has a measuring lever; a lifting member attached to the measuring lever of the tension gauge, the lifting member having an engagement part that engages with a bonding arm of the bonding machine; and a mounting means for mounting the frame body to the wire bonding machine.

The frame body is mounted to the wire bonding machine via the mounting means. The engagement part of the lifting member is engaged with the bonding arm (or with a part of the bonding arm). Then, the turning member is turned by hand in one direction. As a result of this turning motion, the screw shaft is rotated, and the screw assembly, slider, gauge holder and tension gauge are all raised. As a result, the bonding arm is lifted by the lifting member, and the bonding load value is displayed on the tension gauge. The voltage of a linear motor which applies the load to the bonding arm is adjusted accordingly so that the value on the tension gauge becomes equal to a set value.

DETAILED DESCRIPTION OF THE INVENTION

One embodiment of the present invention will be described below with reference to FIGS. 1 through 5.

The structure of a wire bonding machine on which the measuring device of the present invention is mounted will be described first.

Figure 1:
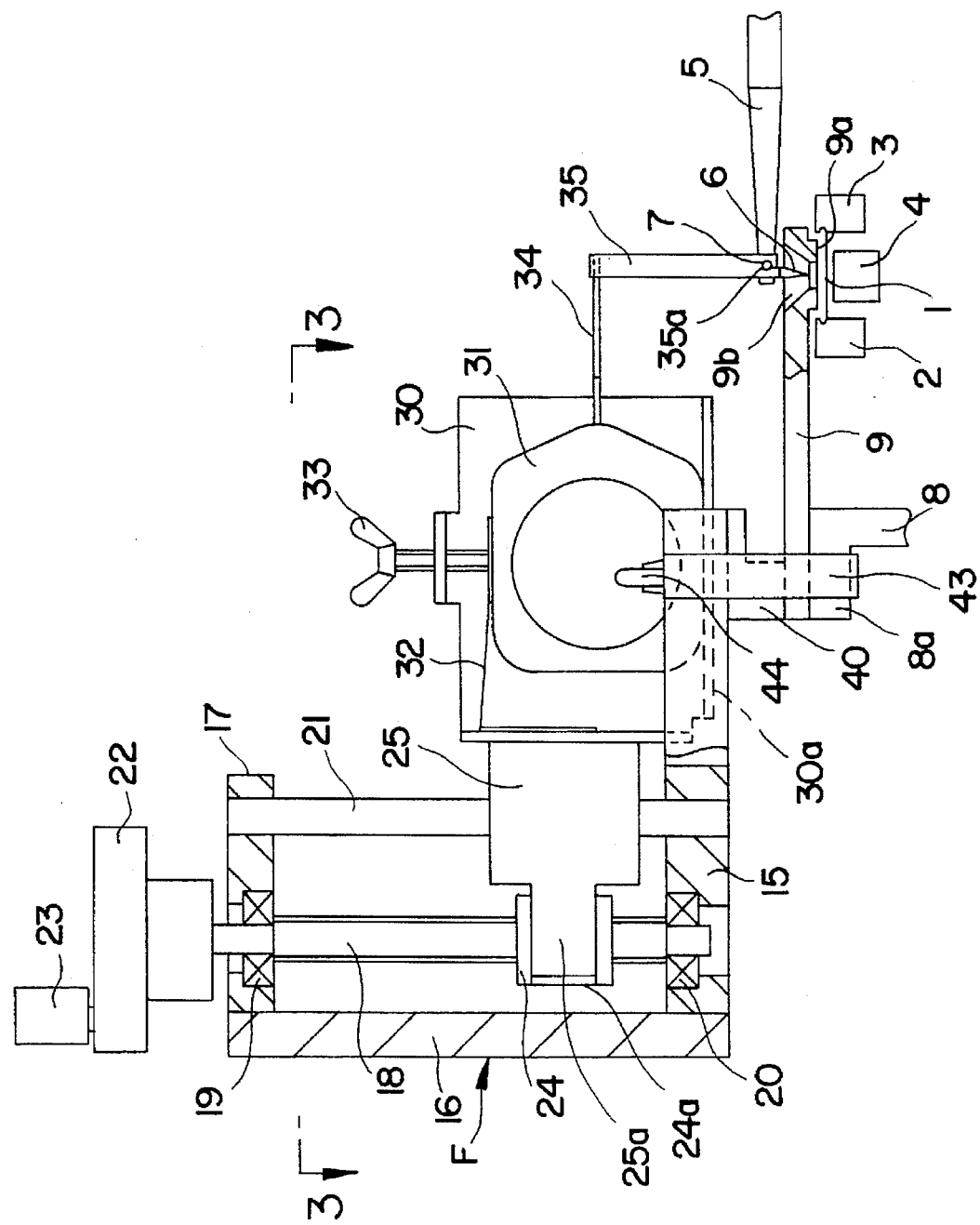
FIG. 1 is a partially cut-away sectional front view of one embodiment of the bonding load measuring device according to the present invention.

As shown in FIG. 1, the bonding machine has a heating block 4 for heating a lead frame 1 between guide rails 2 and 3 which guide the lead frame 1. The heating block 4 is movable vertically. A bonding arm 5 is located above the guide rail 3, and a capillary 6 is attached to the tip end of the bonding arm 5 by a capillary fastening screw 7 so as to be above the heating block 4.

A support column 8 for supporting a cover attachment (not shown) of the bonding machine is located on one side of the guide rail 2, and a lead frame retaining cover 9 is fixed to the top surface of the support column 8. The frame retaining cover 9 has a retaining project 9a for positioning the lead frame 1. In addition, the frame retaining cover 9 has a bonding window 9b. The capillary 6 is brought into this bonding window 9b when the bonding is performed.

The bonding load measuring device of the present invention will be described below in detail.

A frame body F for the bonding load measuring device is made of a base plate 15, a side plate 16 and a supporting plate 17. The side plate 16 is fastened to a base plate 15 vertically, and a supporting plate 17 is fastened to the upper end of the side plate 16. The supporting plate 17 is parallel to the base plate 15.

A screw shaft 18 is installed in the frame body F. In other words, the screw shaft 18 is supported by the base plate 15 and the supporting plate 17 via bearings 19 and 20 in a manner that the screw shaft 18 is rotatable inside the frame body F. A turning member 22 is fastened to the upper end of the screw shaft 18, and a turning handle 23 is attached to the turning member 22. Inside the frame body F, there is also provided a guide rod 21. The guide rod 21 is supported by the supporting plate 17 and base plate 15 so as to be parallel to the screw shaft 18.

A screw assembly 24 is provided on the screw shaft 18. The screw assembly 24 is formed with a thread on its side surfaces so as to engage with the screw shaft 18. A slider 25 is provided on the guide rod 21 in a manner that the slider 25 is movable vertically. The slider has a screw holder 25a. The screw holder 25a is brought into cut-out grooves 24a of the screw assembly 24 which are formed on one end of the screw assembly 24. Thus, when the screw shaft 18 is rotated, the screw assembly 24 can be moved up and down and so can the slider 25.

A gauge holder 30 is attached to the slider 25, and a tension gauge 31 is installed in the gauge holder 30. The gauge holder 30 has a plate spring 32. The plate spring 32 presses the tension gauge 31 against the bottom plate 30a of the gauge holder 30, thus holding the tension gauge 31 in the gauge holder 30. The gauge holder 30 includes a holding screw 33 at the top. The holding screw 33 presses the plate spring 32 against the tension gauge 31. Thus, the tension gauge 31 is removable from the gauge holder 30 by way of the plate spring 32 and holding screw 33.

The tension gauge 31 has a measuring lever 34, and a lifting member 35 is attached to the end of this measuring lever 34. The lifting member 35 has an engagement hole 35a at the bottom so that the engagement hole 35a can be engaged with the capillary fastening screw 7 of the capillary 6.

Figure 3:
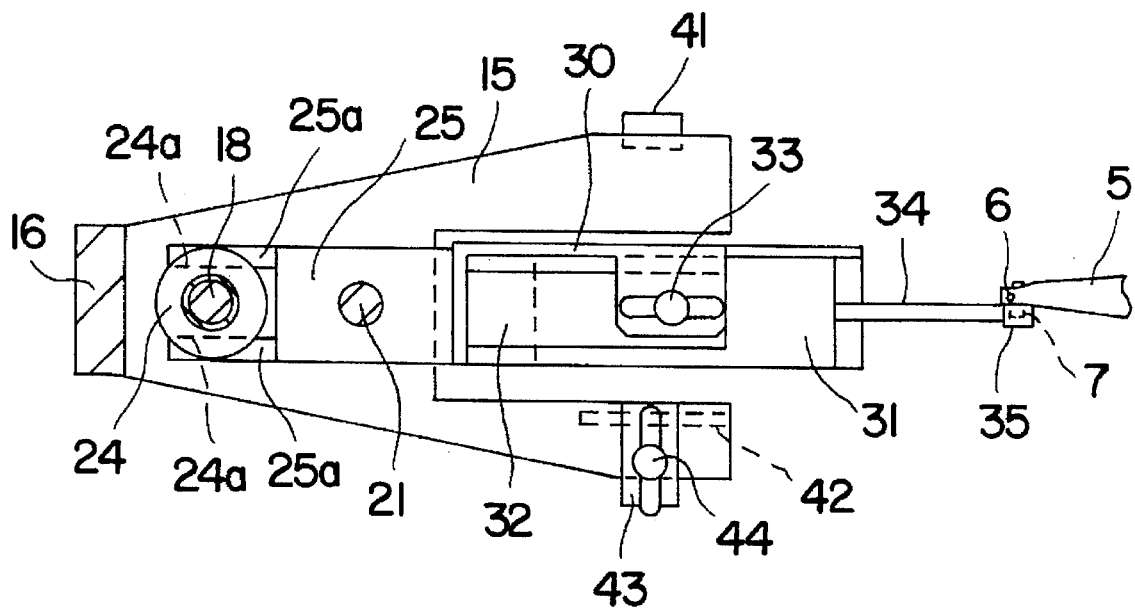
FIG. 3 is a cross section taken along the line 3—3 in FIG. 1.

As best seen in FIG. 3, the far side of the base plate 15 from the side plate 16 is bifurcated. The gauge holder 30 is moved up and down between the bifurcated end of the base plate 15.

Furthermore, as seen in FIG. 1, a carrying plate 40 which is carried on the retaining cover attachment support column 8 is attached to the undersurface of the bifurcated part of the base plate 15.

Figure 2:
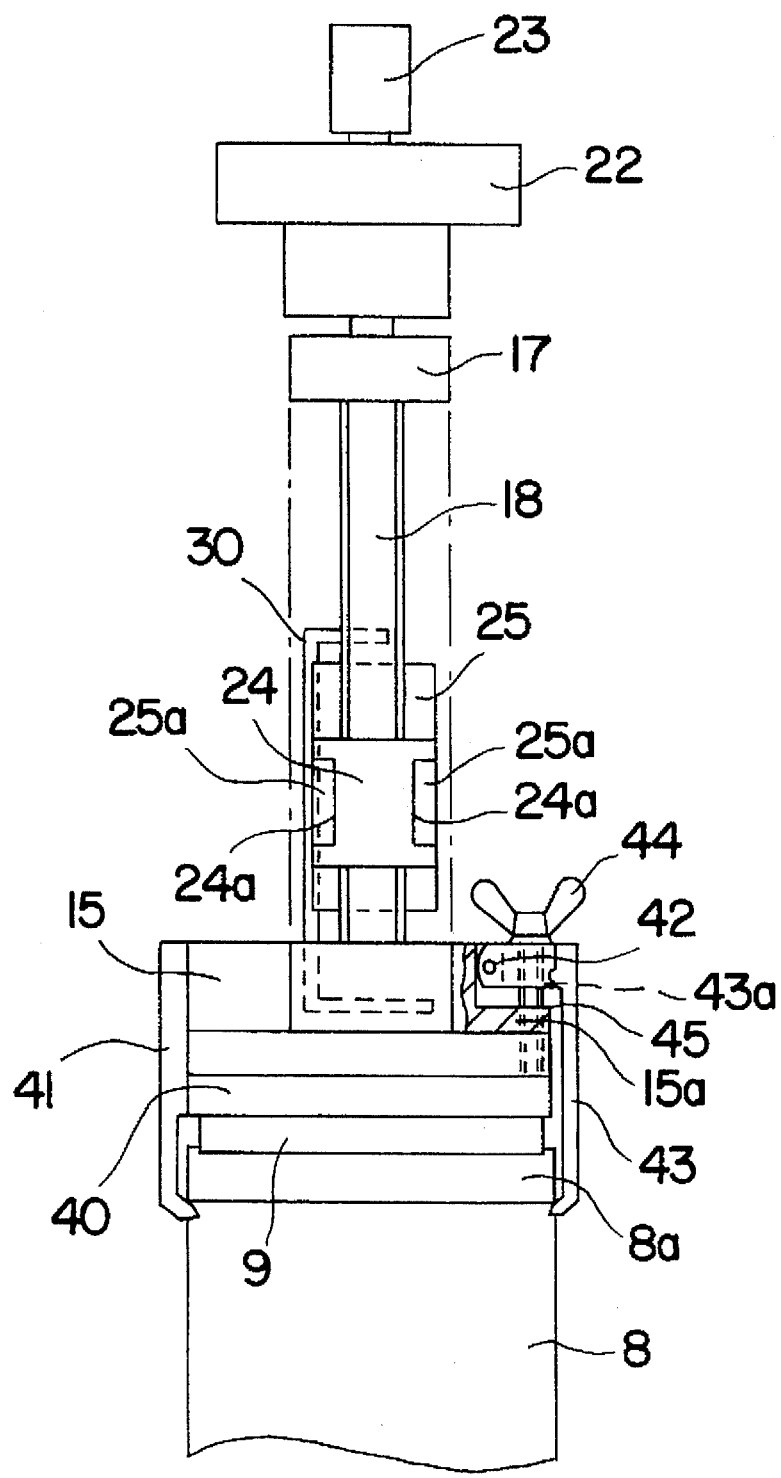
FIG. 2 is a left-side view thereof.

In addition, as seen in FIG. 2, on one side surface of the bifurcated part of the base plate 15, a fixed retainer 41 is provided. The fixed retainer 41 can engage, at its bottom, with the undersurface of a projecting part 8a of the retaining cover attachment support column 8.

Figure 4:
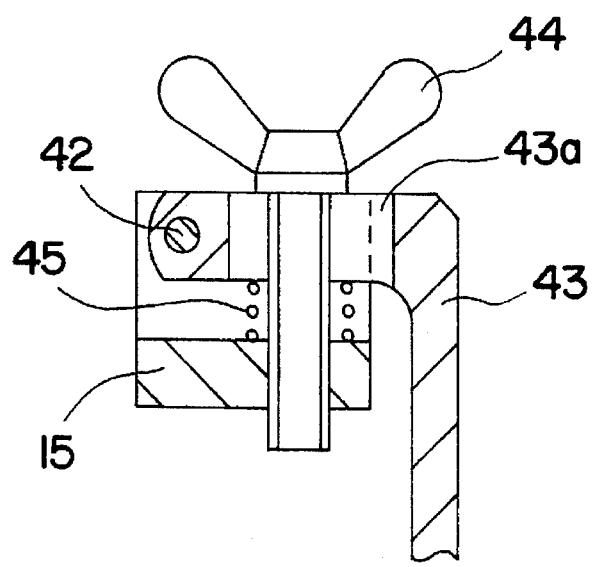
FIG. 4 is shows a cross section of a pivotal retainer used in the measuring device.
Figure 5:
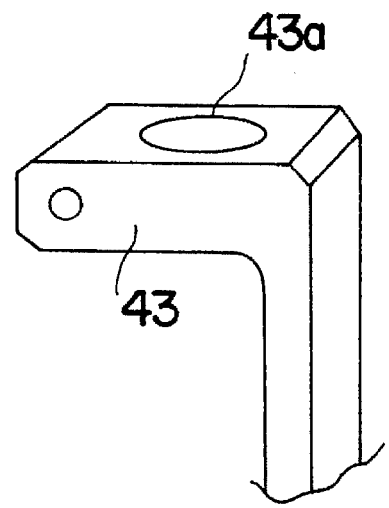
FIG. 5 is a perspective view of the pivotal retainer.
Figure 6:
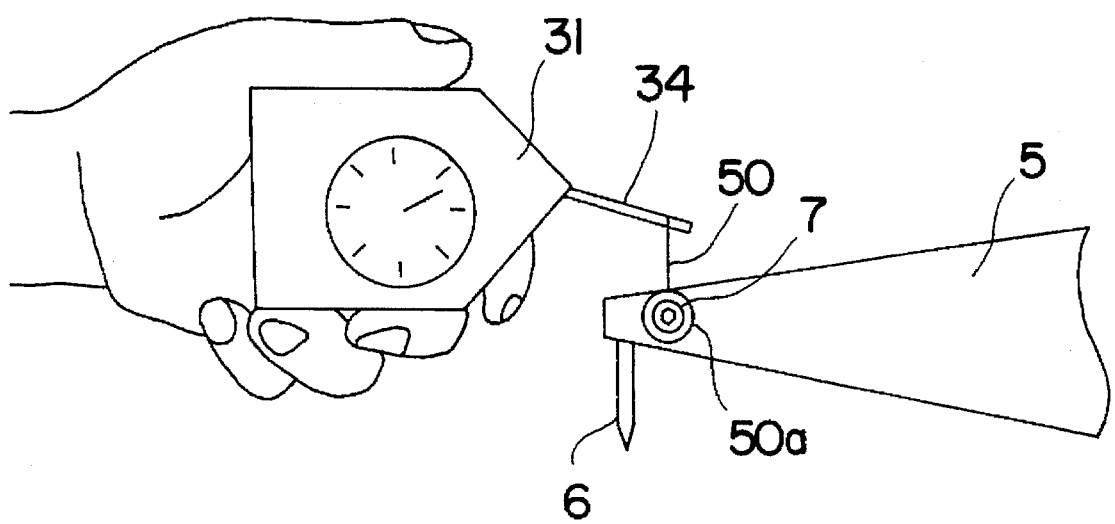
FIG. 6 shows the method of measuring the bonding load performed conventionally.

On another side of the bifurcated part of the base plate 15, a pivotal retainer 43 is provided. The pivotal retainer 43 is pivotable on a pin 42 that is provided in the bifurcated part of the base plate 15. The pivotal retainer 43 is engageable, at its bottom, with the undersurface of the projecting part 8a of the retaining cover attachment support column 8. As seen in FIG. 5, a horizontal slot 43a is formed in the pivotal retainer 43. In addition, as shown in FIG. 4, a retaining screw 44 is inserted into the horizontal slot 43a in a manner that the screw 44 is screw-engageable with the jaw 15a of the base plate 15. A spring 45 is installed between the jaw 15a of the base plate 15 and the pivotal retainer 43. With this spring 45, the pivotal retainer 43 is pushed to pivot and opens as shown by the dotted lines in FIG. 2 when the retaining screw 44 is loosened. The retainers 41 and 43, the pin 42 and the retaining screw 44 make a mounting means for mounting the frame body F to the wire bonding machine.

In use, the bonding load measuring device is first mounted to the projecting part 8a of the retaining cover attachment support column 8. The measuring device is mounted with the retaining screw 44 loosened. In other words, when the retaining screw 44 is loosened, the pivotal retainer 43 is caused to pivot toward the outside about the pin 42 so as to open by the spring 45. The carrying plate 40 is positioned on the retaining cover attachment support column 8, and the base plate 15 is moved sideways so that the fixed retainer 41 engages with the undersurface of the projecting part 8a of the retaining cover attachment support column 8. Then, the retaining screw 44 is tightened. As a result, the pivotal retainer 43 is pushed by the retaining screw 44 and pivots back about the pin 42 and engages at the bottom with the undersurface of the projecting part 8a of the retaining cover attachment support column 8.

The frame body F of the bonding load measuring device is thus mounted on the retaining cover attachment support column 8 of the bonding machine.

Once the frame body F has been thus mounted, the turning handle 23 is turned by hand so that the engagement hole 35a of the lifting member 35 comes to face the capillary fastening screw 7. This is done via the turning handle 23. In other words, the turning handle 23 is turned in one direction, causing the screw shaft 18 to be rotated. When the screw shaft 18 is rotated, the screw assembly 24, slider 25, gauge holder 30 and tension gauge 31 are moved upward or downward. The turning handle 23 is rotated until the engagement hole 35a of the lifting member 35 at the end of the measuring lever 34 faces the capillary fastening screw 7. When the engagement hole 35a is moved to face the capillary fastening screw 7, the lifting member 35 is pushed by hand so that the engagement hole 35a engages with the capillary fastening screw 7.

Then, the turning handle 23 is turned in the reverse direction so that the lifting member 35 is raised. When the lifting member 35 is raised, the bonding arm 5 is lifted by the lifting member 35, and the bonding load of the bonding arm 5 is shown on the tension gauge 31. The bonding load thus obtained is adjusted by changing the voltage of a linear motor (not shown) until the bonding load value matches a set value.

As seen from the above, by turning the turning handle 23, the tension gauge 31 is raised and lowered mechanically so as to perform the measurement of the bonding load. Since the bonding load can be corrected while watching the measured value, setting of the bonding load can be done easily and quickly and precisely. Furthermore, no measurement errors occurs that would be derived from the differences among individual workers performing the measurement. Thus, the reliability is high.

In the above embodiment, the bonding load measuring device is mounted on the retaining cover attachment support column 8 of the wire bonding machine; however, the mounting position is not limited to the retaining cover attachment support column 8. For instance, the bonding load measuring device can be mounted to the operating panel (not shown) that is located on the front side of the wire bonding machine.

Furthermore, in the above embodiment, the fixed retainer 41 and pivotal retainer 43 are used as a means for fastening or mounting the bonding load measuring device in place. However, magnets, for example, can be used as a fastening or mounting means.

Moreover, in the above embodiment, the engagement hole 35a is provided at the end of the lifting member 35 so that this hole 35a is brought so as to be engaged with the capillary fastening screw 7 for lifting the capillary 6. However, the present invention is not limited to this structure. A lifting member having an L-shaped bent end can be used instead so that this bent end engages with the undersurface of the bonding arm 5 or the tip end of the capillary 6.

In addition, the gauge holder 30 can be mounted directly to the screw assembly 24 and not to the slider 25.

As described above, in the present invention, the bonding load measurements are performed via a bonding load measuring device, and this measuring device includes a frame body, a screw shaft rotatable in the frame body, a turning member for turning the screw shaft by hand, a screw assembly engaged with the screw shaft so as to be moved vertically on the screw shaft, a slider provided on a guide rod and connected to the screw assembly so as to be moved together with the screw assembly, a gauge holder attached to the slider for setting therein a tension gauge, a hook attached to the measuring lever of the tension gauge and has an engagement part that engages with the bonding arm, and a fastening means for mounting the frame body to the wire bonding machine. Accordingly, the reliability of the measured bonding load is high, and the time required for setting the bonding load can be short.

I claim:

1. A wire bonding load measuring device for measuring a pressing force for bonding a bonding wire to a connection means of a semiconductor device in a wire bonding machine, said device comprising: a frame body detachably coupled to said wire bonding machine; a screw shaft which rotatably is supported on said frame body so that said screw shaft is free to rotate; a turning member for turning said screw shaft by hand; a screw assembly which is screw-engaged with the screw shaft and caused to move up and down by a rotation of said screw shaft; a slider which moves upward and downward together with the screw assembly; a gauge holder fastened to said slider; a tension gauge detachably installed in said gauge holder in such a manner that said tension gauge can be freely installed and removed; a hook attached to a measuring lever of said tension gauge, said hook having an engagement part that is coupled to a bonding arm; and a mounting means for detachably mounting said frame body to said wire bonding machine;

whereby said pressing force for bonding said bonding wire of a capillary mounted on said bonding arm is measured by rotating said screw shaft.

* * * * *